United States Patent [19]

Buck

[11] Plant 4,225

[45] Mar. 21, 1978

[54] ROSE PLANT NAMED BUCBI

[75] Inventor: Griffith J. Buck, Ames, Iowa

[73] Assignee: Iowa State University Research Foundation, Ames, Iowa

[21] Appl. No.: 749,540

[22] Filed: Dec. 10, 1976

[51] Int. Cl.[2] ..... A01H 5/00

[52] U.S. Cl. ..... Plt./18

[58] Field of Search ..... Plt./1, 18–19, Plt./26–27

*Primary Examiner*—Robert E. Bagwill

*Attorney, Agent, or Firm*—Chas. W. Rummler

[57] ABSTRACT

A new variety of everblooming rose bush distinguished by its tolerance of cold winter temperatures, its profuse production of large pink flowers which bloom continuously during the growing season, and its utility either as a low everblooming shrub or as a mass-effect, low maintenance bedding plant.

1 Drawing Figure

BACKGROUND OF THE NEW PLANT

My new variety of rose plant originated as a seedling resulting from breeding efforts carried on by me since 1949 at Iowa State University with the object of producing winter-cold resistant everblooming garden roses suitable for use either as bedding plants or small shrubs, the new plant resulting from a cross of an unnamed seedling derived from "Applejack" (unpatented); "Dean Collins", P.P. 1279; "Queen Elizabeth", P.P. 1259; "Independence", P.P. 1036; and "Improved Lafayette" (unpatented) as the seed parent, and "Prairie Princess" (unpatented) as the pollen parent.

This new rose plant was discovered by me in 1969 as a promising fulfillment of my before mentioned objective and asexual propagation of this plant carried on by me and under my direction through successive generations by bud grafting has demonstrated that its new and advantageous characteristics hold true from generation to generation and appear to be firmly fixed. Propagation of this new plant is now being carried on by bud grafting at Ames, Iowa, and at West Grove, Pa.

DESCRIPTION OF THE DRAWING

My new rose plant is illustrated by the accompanying full color photographic drawing which shows the flowers in full bloom, as well as buds and partially opened flowers, and specimens of the leaves, the colors shown being as nearly true as is possible to obtain by conventional photographic procedures and considering the delicate pink flower coloration.

DESCRIPTION OF THE NEW PLANT

The following is a detailed description of my new rose plant with color designations according to the R.H.S. Colour Chart, published by The Royal Horticultural Society of London, England, in collaboration with The British Colour Council.

THE PLANT

Origin: Seedling.

Parentage:

*Seed parent.*—"Applejack" (unpatented) × [("Dean Collins" × "Queen Elizabeth") × ("Independence" × "Improved Lafayette")].

*Pollen parent.*—"Prairie Princess" (unpatented).

Classification:

*Botanic.*—Rosa hybrida.

*Commercial.*—Shrub Rose.

Form: Bush.

Height: 1 meter. Taller in areas with a longer growing season.

Growth: Vigorous.

Habit: Sturdy and upright. Branching and later spreading.

Foliage: Quantity — abundant.

*Leaves.*—Form: Compound — Odd pinnate. Size: 10 to 13 cm. long.

*Leaflets.*—5 to 7 in number. Shape: Obovate to round-ovate. Color: Upper side — Intermediate of RHS 147A (Woodpecker Green) and RHS 147B (Peridot Green). Under side — RHS 147C (Iris Green). Texture: Leathery. Aspect: Smooth and semi-glossy. Ribs and veins: Not prominent. Petioles: 5 to 7 mm. long.

*Rachis.*—4.0 to 6.3 cm. long.

*Spines and prickles.*—8 to 11 mm. long. Color: RHS 147C (Light Brown-Orange) with some 174A and 174B.

THE BUD

Form: Ovoid, long and pointed.

Size: Medium-large.

*Diameter.*—2.4 to 2.7 cm.

*Depth.*—3.5 to 4.5 cm.

Opening rate: Bud opens slowly.

Color:

*When sepals first divide.*—RHS 57C (Rose Beige).

*When sepals unfurl.*—RHS 57B (Rose Bengal).

Sepals: Spear-shaped and curl back as bud opens.

*Color.*—Inside surface — RHS 146B at tip, passing to RHS 147 at base. Outside surface — RHS 146D tinted red at tips and edges.

Calyx: Size — large.

*Shape.*—Funnel-shaped, becoming globular.

*Splitting.*—Calyx does not split.

*Aspect.*—Smooth.

Peduncle: Length — 2.0 to 2.5 cm.

*Strength.*—Quite strong.

*Hairs and prickles.*—Slightly prickly.

*Color.*—RHS 146C tinted with red on side exposed to the sun.

THE FLOWER

Blooming habit: Continuous, blooming profusely from early to late throughout the growing season.

Size: Very large.

*Diameter.*—10.5 to 12.0 cm.

*Depth.*—3.5 to 4.0 cm.

Borne: Singly and in clusters.

Shape: When bloom first opens — shallow cup becoming flat as flower matures.

Petalage: Number of petals — 15 to 20 including petaloids.

*Arrangement.*—Open.

*Form.*—Round-ovate.

*Color.*—Outer petals — RHS 57D (Light Rose Bengal) with RHS 154B (Chartreuse Green) over white at base and spreading over the petal color. Inside petals — RHS 57C (Rose Bengal). Reverse side — RHS 58D (Light Bengal Rose).

*Texture.*—Soft.

*Appearance.*—Satiny.

Petaloids: 3 to 5 in number.

*Size.*—Medium large.

*Color.*—RHS 57C (Rose Bengal).

Pedicel: 4.5 to 5.0 cm. long, sturdy and upright.

*Color.*—RHS 146C (Medium Green).

Discoloration: Color lightens after full bloom.

Effect of weather: Not appreciable.

Persistence: Petals fall cleanly.

Disease resistance: Tolerant of blackspot and powdery mildew where those diseases are prevalent.

Fragrance: Moderately strong and sweet.

Lasting quality:

*On plant.*—2 to 7 days.

*As cut flower.*—3 to 4 days.

REPRODUCTIVE ORGANS

Stamens:

*Anthers.*—Numerous. Arrangement: circular. Length: 4 to 6 mm.

*Filaments.*—1.2 to 1.4 cm. long. Color: RHS 5B (Dresden Yellow).

*Pollen.*—Color — RHS 5A (Dresden Yellow).

Pistils: Numerous in number.

*Styles.*—1.0 to 1.4 cm. long.

*Stigmas.*—Color — RHS 5B (Dresden Yellow).

Fruit: Fertile.

*Shape.*—Ovoid to round.

*Color at maturity.*—RHS 31A (Burnt Orange) to RHS 31C (Mars Orange) tinged green.

Although this new rose plant does not conform to the present garden rose classes, it does offer an everblooming rose bush which is reasonably tolerant of cold winter temperatures without resort to excessive winter-protection methods. Because of this trait, and its tolerance to Blackspot and Powdery Mildew diseases, the new plant is particularly useful as an everblooming shrub or as a mass effect, low-maintenance bedding plant capable of a profuse and continuous production of very large flowers which can be cut and have an acceptable use-life.

I claim:

1. The new and distinct variety of rose plant substantially as herein shown and described, characterized by its tolerance to cold winter temperatures, its continuous and profuse vase-life production of very large, delicate pink flowers throughout the growing season, and its adaptability for use as a low shrub or as a mass effect, low-maintenance bedding plant.

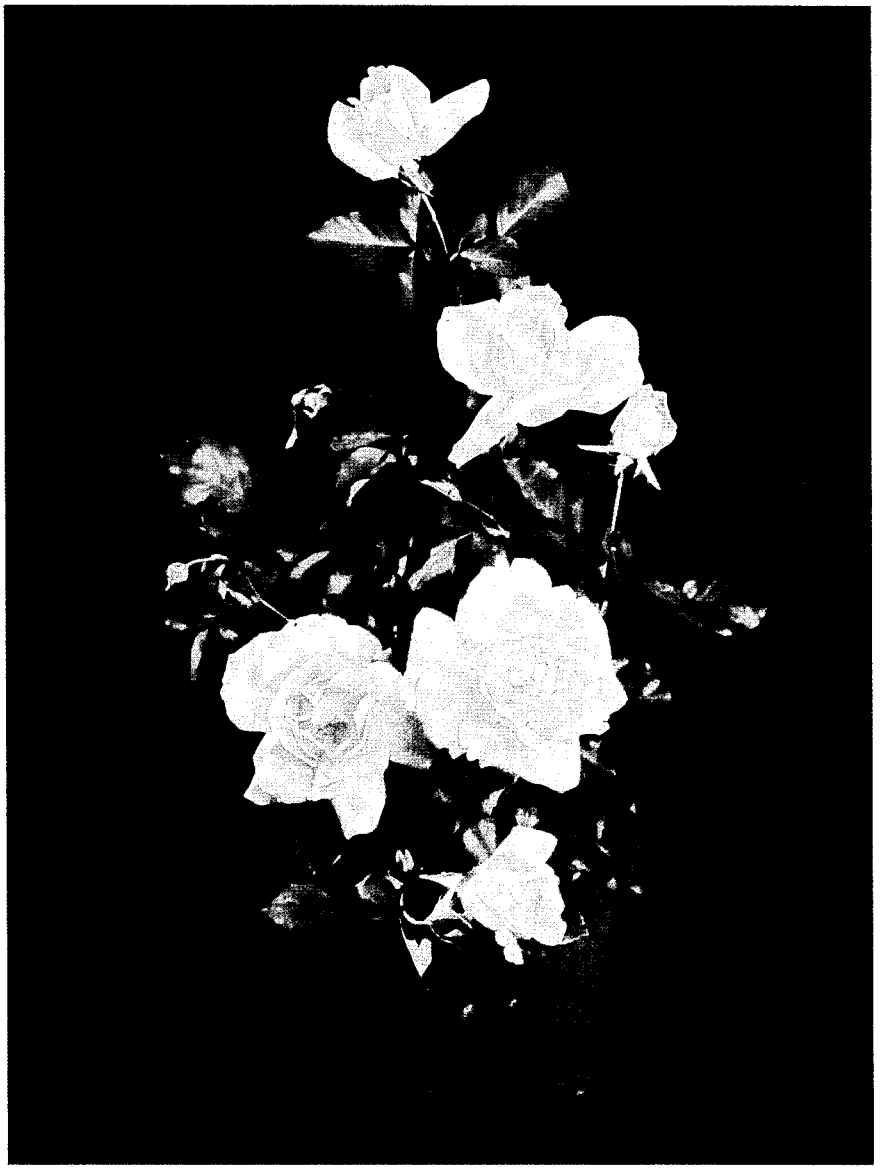

* * * * *